United States Patent [19]
Huxham

[11] Patent Number: 6,017,374
[45] Date of Patent: Jan. 25, 2000

[54] GAS TREATMENT DEVICES

[75] Inventor: Laurence Stanmore Huxham, Ashford, United Kingdom

[73] Assignee: Smiths Industries Public Limited Company, London, United Kingdom

[21] Appl. No.: 09/019,687

[22] Filed: Feb. 6, 1998

[30] Foreign Application Priority Data

Feb. 28, 1997 [GB] United Kingdom .................... 9704241

[51] Int. Cl.⁷ ............................. B01D 50/00; A62B 7/10
[52] U.S. Cl. ............................. 55/315.2; 55/331; 55/332; 55/418.1; 55/424.2; 55/DIG. 35; 128/201.13
[58] Field of Search .................................. 55/308, 315.1, 55/320, 331, 332, 418, 418.1, 529, 434.2, 462, 463, 315.2, DIG. 35; 128/201.13, 205.29

[56] References Cited

U.S. PATENT DOCUMENTS

| | | |
|---|---|---|
| 3,815,754 | 6/1974 | Rosenberg . |
| 3,870,488 | 3/1975 | Arndt et al. . |
| 4,014,671 | 3/1977 | Andro et al. . |
| 4,836,834 | 6/1989 | Steele . |
| 5,195,527 | 3/1993 | Hicks . |
| 5,213,096 | 5/1993 | Kihlberg et al. . |
| 5,320,096 | 6/1994 | Hans . |
| 5,549,722 | 8/1996 | Zemaitis et al. . |
| 5,590,644 | 1/1997 | Rosenkoetter . |
| 5,599,448 | 2/1997 | Spearman . |
| 5,814,117 | 9/1998 | Mochida . |

FOREIGN PATENT DOCUMENTS

| | | |
|---|---|---|
| 0311968A | 4/1989 | European Pat. Off. . |
| 0707827A | 4/1996 | European Pat. Off. . |
| 2126499 | 3/1984 | United Kingdom . |
| 2231509A | 11/1990 | United Kingdom . |
| 2267661 | 12/1993 | United Kingdom . |
| 2267840 | 12/1993 | United Kingdom . |
| WO 93/16749 | 9/1993 | WIPO . |

Primary Examiner—David A. Simmons
Assistant Examiner—Fred Prince
Attorney, Agent, or Firm—Pollock, Vande Sande & Amernick

[57] ABSTRACT

A combined filter and HME has a rectangular housing with an inlet port and an outlet port. A pleated filter element is located in the housing towards the outlet port and an HME element is located towards the inlet port. An oval deflector between the HME element and the inlet port is oriented with its longer axis aligned with the shorter lateral dimension of the housing, so that gas from the inlet is deflected preferentially along the longer lateral dimension of the housing, thereby giving a more evenly distributed gas flow over the surface of the HME element.

11 Claims, 2 Drawing Sheets

6,017,374

GAS TREATMENT DEVICES

BACKGROUND OF THE INVENTION

This invention relates to gas treatment devices, such as filters or heat and moisture exchange devices (HMEs).

Medical filters and HMEs have a housing with couplings at opposite ends and a filter or HME element located in the housing, between its ends, so that gas flowing through the housing, between the couplings, passes through the element. These devices should have a maximum efficiency, with a minimum resistance to flow, a minimum dead space and low overall bulk. The dead space can be reduced by reducing the volume in the housing on either side of the element but this has the effect of hindering gas flow over the surface of the element, so that the gas flows mainly through the center of the element. In order to spread the gas flow more evenly over the element, devices often include a deflector located just above the element, in-line with the coupling on the inlet side, or, where the device is bidirectional, on both sides. The deflector has a conical or trumpet shape, as described in GB2231509, and is symmetrical about the axis of the device between the couplings. Such deflectors can improve the performance of those devices having a circular shape but, where the device is of a non-circular shape, such as rectangular or elliptical, the deflector may fail to distribute gas evenly to the outer parts of the element.

SUMMARY OF THE INVENTION

It is an object of the present invention to provide an improved gas-treatment device.

According to the present invention there is provided a gas treatment device including a housing having an inlet port and an outlet port, a gas treatment element located in the housing between the two ports and a gas flow deflector located in the housing between the element and the inlet port, the element having a surface with an asymmetric shape presented to the gas flow, and the gas flow deflector having an asymmetric shape about the axis of the inlet port so as to distribute gas more equally over the surface of the element.

The housing and gas treatment element are preferably rectangular in section. The deflector is preferably oval in lateral section with a convex surface presented to the inlet port, the longer lateral axis of the deflector being aligned with the shorter lateral dimension of the gas treatment element. The longer lateral dimension of the gas flow deflector is approximately twice that of its shorter lateral dimension. The gas treatment element may include a filter, which may be pleated with pleats extending parallel to the longer lateral dimension of the housing. The gas treatment element may include an HME element Where the device includes both a filter and an HME element, the filter is preferably located at one end of the housing, the HME element being located at the opposite end. The HME element is preferably located towards the inlet port and the filter towards the outlet port.

A combined filter and HME, in accordance with the present invention, will now be described, by way of example, with reference to the accompanying drawings.

DETAILED DESCRIPTION OF THE PREFERRED EMBODIMENTS

Figure 1:
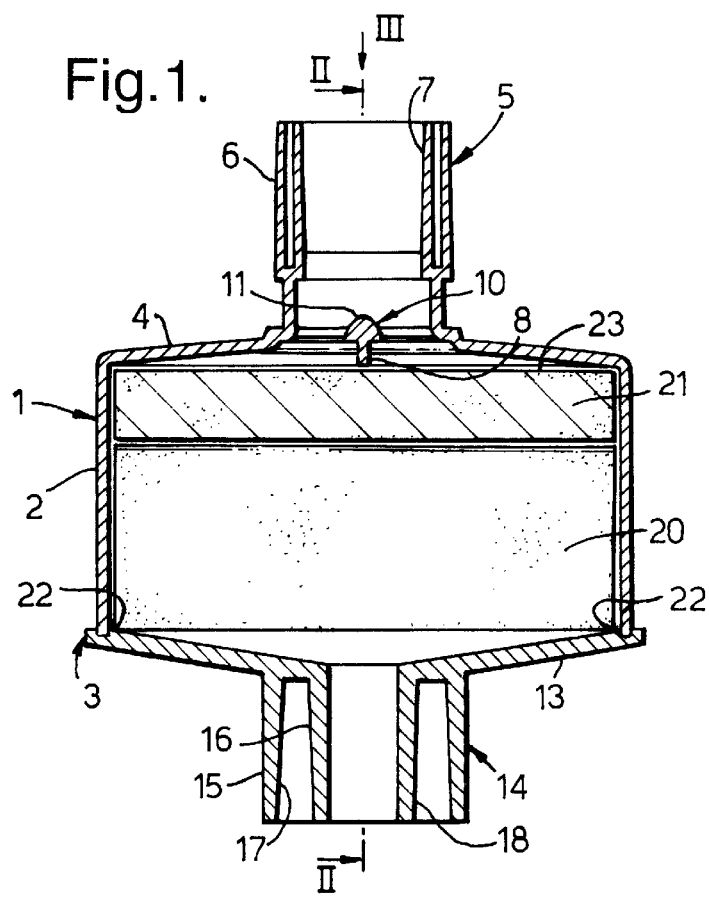
FIG. 1 is a sectional side elevation view of the device.
Figure 2:
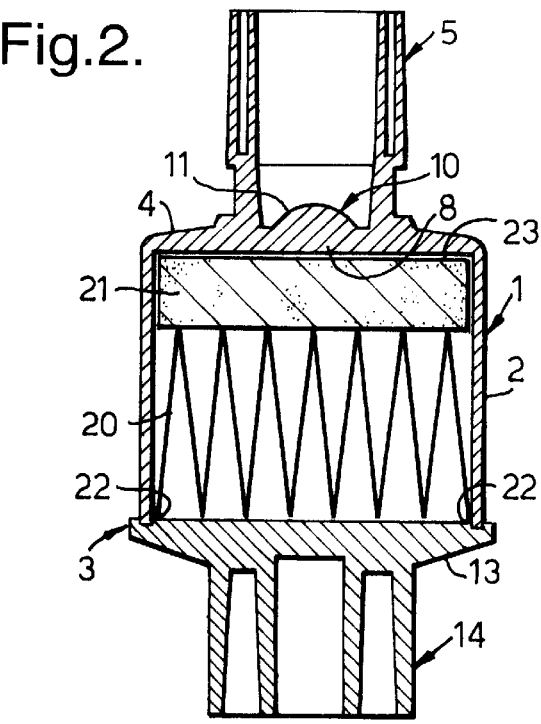
FIG. 2 is a sectional transverse elevation view along the line II-II of FIG. 1.
Figure 3:
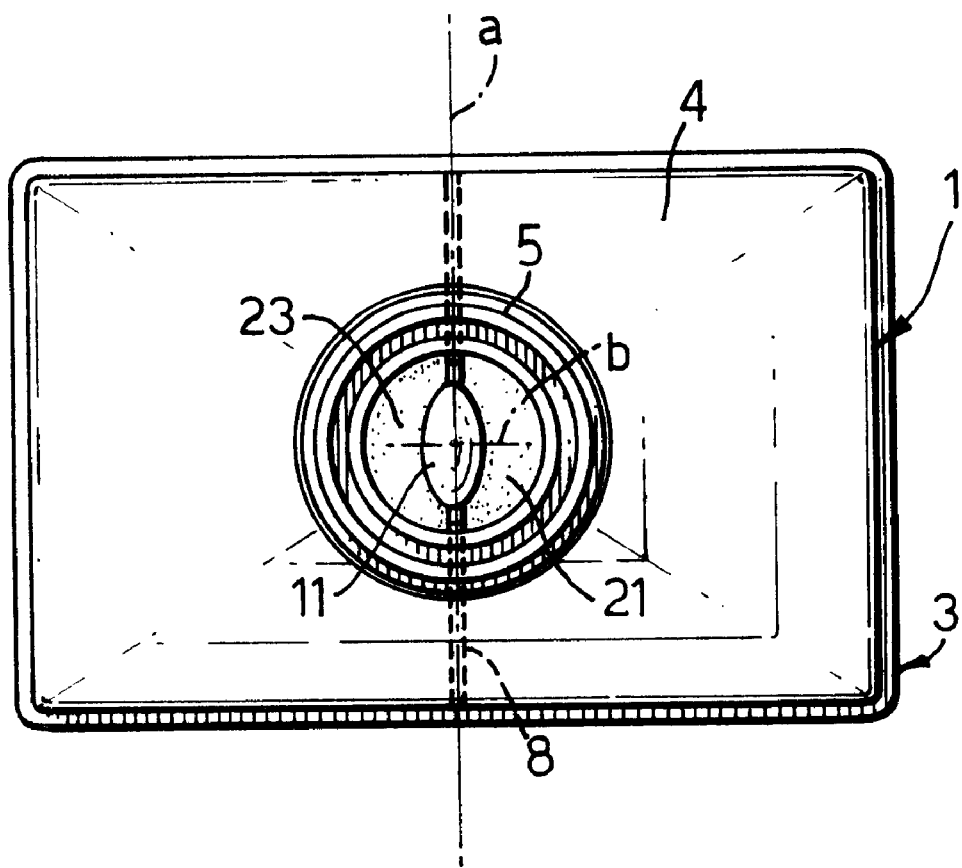
FIG. 3 is a plan view of the device along the arrow III of FIG. 1.

The filter/HME has an outer housing 1 in two parts: an upper part 2 and a lower part 3. The upper part 2 is of rectangular shape with an internal width (that is, its longer lateral dimension) of about 65mm and a depth (its shorter lateral dimension) of about 40mm. The upper part 2 has a roof 4 with a shallow dome and a patient end, inlet port 5 located centrally on the roof. The inlet port 5 is circular in section with an internal diameter of about 14mm and an external male taper 6; its inside has a female taper 7. A thin strut 8 extends laterally across the underside of the roof 4 and diametrically across the lower end of the port 5. The strut 8 supports a flow deflector 10 of novel shape. The deflector 10 has an oval lateral section, that is, when viewed in plan, being about 11mm long and 5mm wide, so that its longer lateral dimension is about twice its shorter dimension. The longer axis "a" of the oval is aligned with the depth of the housing 1 (that is, its shorter lateral dimension), the shorter axis "b" being aligned with the width of the housing (that is, its longer lateral dimension). The upper surface 11 of the deflector 10 is convex, when viewed from above, and projects about 3mm above the upper surface of the strut 8.

The lower end of the upper part 2 of the housing 1 is open and is joined to the upper end of the lower part 3. The lower part 3 has a domed rectangular plate 13, similar in shape to that of the roof 4, the outer edge of the plate 13 being bonded to the lower end of the upper part. The lower part 3 also has an outlet, machine end port 14 located centrally of the plate 13 and in line with the patient end port 5. The outlet port 14 has two concentric sleeves 15 and 16. The inner surface 17 of the outer sleeve 15 has a female taper; the outer surface 18 of the inner sleeve 16 has a male taper.

The filter/HME includes a filter element 20 and an HME element 21 within the housing 1. The filter element 20 is of a pleated paper, with the pleats extending parallel to the width of the housing, and is located at the lower end of the housing 1, being sealed around its edge 22 to the inside of the housing. Other conventional filters could be used. The HME element 21 may be of any conventional kind, and sits on top of the filter element 20, between it and the inlet port 5. The two elements 20 and 21 are of rectangular shape in lateral section, conforming to the inside shape of the housing. The upper surface 23 of the HME element 21 abuts the lower surface of the strut 8, which ensures that there is clearance between the HME element and the underside of the roof 4.

In use, the filter/HME is connected in a patient breathing circuit (not shown), with the port 5 coupled to a tracheal tube or mask, and with the other port 14 connected to ventilation or anaesthesia apparatus, or left open to atmosphere if the patient is breathing spontaneously. When the patient exhales, gas flows through the port 5 over the surface 11 of the deflector 10. The shape of the deflector 10 is such that less gas is diverted in directions along the major axis "a" of the deflector, and more gas is diverted in directions along its minor axis "b". The orientation of deflector 10 and its shape ensure that gas is deflected preferentially along the longer lateral dimension of the housing than the shorter dimension. This ensures that gas flow to that part of the surface 23 of the HME element 21 furthest from the inlet port 5 is made more equal to that over the central region of the element. Some of the heat and moisture in the exhaled gas is taken up by the HME element 21. Gas then flows through the filter element 20 and out of the machine port 14. The filter element 20 also acts in part to retain some heat and moisture of the exhaled gas.

Inhaled gas flows in through the machine port 14 and through the filter element 20. In most cases, there is less need for a deflector at the machine end of the device because the pleats help channel gas along the width of the housing. Any bacteria viruses or particles in the incoming gas are filtered out by the filter element 20 before reaching the HME element 21. The filter element 20 also transfers some of its retained heat and moisture to the incoming gas. When the gas passes through the HME element 21, it takes up a part of the heat and moisture in the HME element, so the gas supplied to the patient is filtered, warmed and increased in humidity.

The device described above only has a flow deflector at one end because the pleats of the filter act to channel inspiratory gas across the width of the device, thereby ensuring that it is distributed evenly across the device. In devices with other forms of filter element, or in devices with only an HME element and no filter, where the element does not act to channel gas across the device, however, it might be desirable to have a deflector at both ends of the device.

What I claim is:

1. A gas treatment device comprising: a non-circular housing, said housing having an inlet port and an outlet port; a gas treatment element of non-circular section located in said housing between said ports; and a gas flow deflector located in said housing axially of said inlet port between said element and said inlet port, wherein said element has a surface with an asymmetric shape presented to gas flow from said inlet port, and wherein said gas flow deflector has an asymmetric shape about an axis of said inlet port so as to distribute gas more equally over said surface of said element.

2. A device according to claim 1, wherein said housing and said gas treatment element are rectangular in section.

3. A device according to claim 1 or 2, wherein said deflector is oval in lateral section, wherein said deflector has a convex surface presented to said inlet port, and wherein a longer lateral axis of said deflector is aligned with a shorter lateral dimension of said gas treatment element.

4. A device according to claim 1, wherein said gas flow deflector has a longer lateral dimension approximately twice that of a shorter lateral dimension.

5. A device according to claim 1, wherein said gas treatment element includes a filter.

6. A device according to claim 5, wherein said filter is pleated with pleats extending parallel to a longer lateral dimension of said housing.

7. A device according to claim 1, wherein said gas treatment element includes an HME element.

8. A device according to claim 1, wherein said gas treatment element includes a filter, said filter being located at one end of said housing, and an HME element, said HME element being located at an opposite end of said housing.

9. A device according to claim 8, wherein said HME element is located towards said inlet port and said filter is located towards said outlet port.

10. A gas treatment device comprising: a housing, said housing being of rectangular lateral section and having an inlet port and an outlet port; a gas treatment element located in said housing between said ports, said gas treatment element being of rectangular lateral section; and a gas flow deflector located in said housing axially of said inlet port between said element and said inlet port, wherein said gas flow deflector is of oval shape in section with a convex surface presented to said inlet port, and wherein a longer lateral dimension of said deflector is aligned with a shorter lateral dimension of said gas treatment element so as to distribute gas more equally over a surface of said element.

11. A combined filter and HME comprising: a housing, said housing having a rectangular lateral section and having an inlet port and an outlet port; a filter element located in said housing towards said outlet port; an HME element located in said housing between said filter and said inlet port; and a gas flow deflector located in said housing axially of said inlet port between said HME element and said inlet port, wherein said gas flow deflector is shaped to deflect gas preferentially along a longer lateral dimension of said housing than a shorter lateral dimension so as to distribute gas more equally over a surface of said HME element.

* * * * *